US007195905B2

(12) United States Patent
Kistner et al.

(10) Patent No.: US 7,195,905 B2
(45) Date of Patent: Mar. 27, 2007

(54) ENVELOPED VIRUS VACCINE AND METHOD FOR PRODUCTION

(75) Inventors: Otfried Kistner, Vienna (AT); Manfred Reiter, Vienna (AT); Axel Bruehmann, Vienna (AT); Noel Barrett, Klosterneuburg/Weidling (AT); Wolfgang Mundt, Vienna (AT); Friedrich Dorner, Vienna (AT)

(73) Assignee: Baxter Healthcare S.A., Zurich (CH)

( * ) Notice: Subject to any disclaimer, the term of this patent is extended or adjusted under 35 U.S.C. 154(b) by 0 days.

(21) Appl. No.: 10/006,671

(22) Filed: Dec. 10, 2001

(65) Prior Publication Data

US 2003/0108859 A1 Jun. 12, 2003

(51) Int. Cl.
*C12N 7/02* (2006.01)
*A61K 39/12* (2006.01)

(52) U.S. Cl. .................................. 435/239; 424/218.1
(58) Field of Classification Search ............. 424/218.1; 435/70.1, 236, 239

See application file for complete search history.

(56) References Cited

U.S. PATENT DOCUMENTS

| 4,525,349 A | * | 6/1985 | Montagnon et al. | ........... 424/89 |
| 4,664,912 A | * | 5/1987 | Wiktor et al. | ................. 424/89 |
| 5,789,245 A | * | 8/1998 | Dubensky et al. | ....... 435/320.1 |
| 5,858,658 A | | 1/1999 | Haemmerle et al. | ........... 435/6 |

FOREIGN PATENT DOCUMENTS

| WO | WO 96/17072 A2 | 6/1992 |
| WO | WO 96/15231 | 5/1996 |
| WO | WO 98/45415 | 10/1998 |
| WO | WO 00/03000 | 1/2000 |
| WO | WO 01/23527 | 4/2001 |
| WO | WO 01/92552 A2 | 12/2001 |

OTHER PUBLICATIONS

Harley et al., Ross River Virus Transmission, Infection and Disease: a Cross-Disciplinary Review, Clin. Micro. Reviews 14:909-932, Oct. 2001.*
Aaskov, et al.; *A Candidate Ross River Virus Vaccine: Preclinical Evaluation; Vaccine*; vol. 15, No. 12/13, p. 1396-1404 (1997).
Bahnemann; *Inactivation of Viral Antigens for Vaccine Preparation with Particular reference to the Application of Binary Ethylenimine; Vaccine*; vol. 8, p. 299-303 (1990).
Butler; *Animal Cell Biotechnology*; Ed. R.E. Spier and Griffiths; vol. 3, p. 284-303 (1988).
European Pharmacopoeia; 2.6.8 Pyrogens, p. 1-3 (2001).
Kistner, et al.; *Development of a Mammalinan Cell (Vero) Derived Candidate Influenza Virus Vaccine; Vaccine*; vol. 16, No. 9/10 p. 960-968 (1998).
WHO Study Group; *Acceptability of Cell Substrates for Production of Biologicals; World Health Organization Technical Report Series*; vol. 747, p. 1-29 (1987).
WHO Study Group; *Requirements for the use of Animal Cells as in Vitro Substrates for the Production of Biologicals; World Health Organization Technical Report Series*; vol. 878, p. 19-56 (1998).
Yu, et al.; *Development of a Candidate Vaccine Against Ross River Virus Infection; Vaccine*; vol. 12, No. 12, p. 1118-1124 (1994).

* cited by examiner

*Primary Examiner*—Stacy B. Chen
(74) *Attorney, Agent, or Firm*—Townsend and Townsend and Crew LLP

(57) ABSTRACT

The present invention provides methods of production of a purified enveloped virus antigen. In particular, it provides purified Ross River Virus (RRV) antigens, and vaccines comprising purified, inactivated Ross River Virus (RRV) antigen.

16 Claims, 1 Drawing Sheet

A     1   2   3   4   5

B     1   2   3   4   5

ENVELOPED VIRUS VACCINE AND METHOD FOR PRODUCTION

FIELD OF THE INVENTION

The present invention is directed to methods of production of a purified enveloped virus antigen, for example, Ross River Virus (RRV) antigen, and to a vaccine comprising purified, inactivated Ross River Virus (RRV) antigen, wherein the RRV antigen is free of heterologous nucleic acid and protein contaminants from the cells and the cell culture.

BACKGROUND OF THE INVENTION

Safe vaccine production, particular for human administration requires the growth of large quantities of virus produced in high yields from a host system, as well as efficient purification and inactivation methods. Serum or serum-derived substances such as albumin, transferrin or insulin and/or proteins from animal or human sources added to a cell culture medium may contain undesirable agents that can contaminate the culture and the biological material produced therefrom. One of the major concerns for the production of biologicals, such as vaccines or recombinant products, is the potential risk of contaminants such as Bovine Spongiform Encephalopathy (BSE). Furthermore, the World Health Organization (WHO) encourages the use of agents having an inactivating effect on the biological activity of DNA. On the basis of a study on the potential risks associated with biologicals produced in animal cells, the WHO Study Group concluded that levels at up to 10 ng nucleic acid per purified dose can be considered acceptable (1998, WHO, Technical Report Series No. 878), but levels of less than 100 pg per dose would be preferred. However, most viruses used for vaccine production have not been purified to preserve their sensitive biological activity which is critical for efficacy of the vaccine, because efficient purification methods seem to influence the immunogenicity and antigenicity of the virus. In addition, purification methods currently available for virus or virus antigen do not always remove the cell culture contaminants efficiently. Thus, for each particular virus, an appropriate method has to be developed and adapted to large scale.

Ross River Virus (RRV) is a mosquito borne Alphavirus which causes a disease in humans known as epidemic polyarthritis (EPA). It is endemic in Australia, with more than 5000 cases presenting each year. Currently, there is no existing vaccine, and mosquito control programs have not had any noticeable effect in reducing the incidence of disease.

An experimental candidate RRV vaccine previously developed by Yu et al. (1994, Vaccine 12: 1118–1124) and Aaskov et al. (1997, Vaccine 15: 1396–1404) has been demonstrated to protect mice from challenge with live virus. This vaccine is obtained from the supernatant of infected VERO cells cultivated on a small scale basis in Roller bottles in serum-containing medium. The virus-containing supernatant is centrifuged to remove cellular debris and the supernatant is incubated for virus inactivation with Binary ethylenimine (BEI) under alkali conditions at pH 8.5–9.0. The inactivated virus suspension is subjected to sucrose gradient centrifugation, the band of virus of the gradient interface recovered is resuspended in saline buffer and used for immunization studies in mice. However, in the preparation solely subjected to sucrose-gradient purification without any other treatment, cellular contaminants, such as cellular DNA or proteins, can be still present in the virus preparation.

The candidate BEI-inactivated Ross River Vaccine described, supra, is tested at different concentrations of an adjuvant and without adjuvant in mice. Greater protection is found with the vaccine at higher dose without adjuvant than those with an adjuvant. Even at lower dose the non-adjuvanted vaccine induced significantly higher antibody titers compared to the adjuvanted. Comparative studies on neutralizing antibody titers after a second injection of mice with low antigen concentrations of 0.2 or 2.0 µg of vaccine with and without adjuvant caused researchers to conclude that the adjuvant may suppress at low concentrations the protective component of a secondary immune response to the BEI-inactivated vaccine.

Because of the need for a safe and effective Ross River Virus Vaccine for human administration, large-scale production of virus and efficient purification and inactivation methods are required. The present invention is directed to the large-scale production of Ross River Virus suitable for preparation of a vaccine for administration to humans.

SUMMARY OF THE INVENTION

It is thus an object of the present invention to provide a method for the production of purified Ross River Virus antigen.

It is also an object of the present invention to provide a method of production of a vaccine comprising purified Ross River Virus being suitable for human administration.

DETAILED DESCRIPTION OF THE PREFERRED EMBODIMENTS

Figure 1:
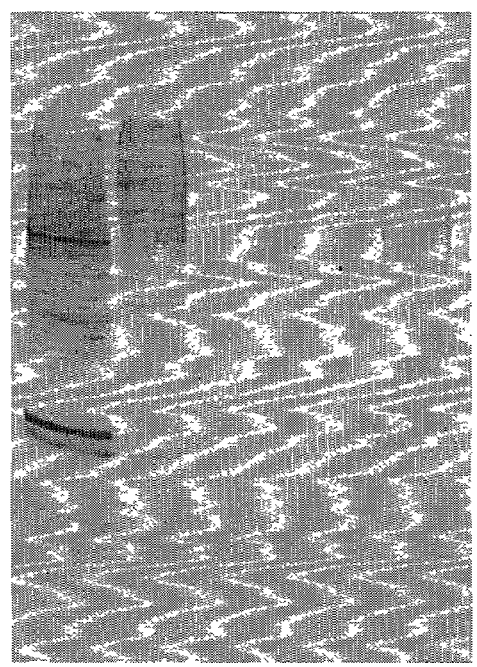
FIG. 1: Western Blot analysis of efficacy of filtration of Ross River Virus harvest on removal of cellular proteins derived from cell culture. A: Detection of VERO cell protein with anti-VERO protein antibodies and B: Detection of Ross River Virus antigen with anti-RRV antibodies. It is shown is in lane 1: VERO cell lysate as control, lane 2: RRV harvest after centrifugation, lane 3: after filtration, lane 4: after BENZONASE endonuclease treatment, lane 5: after sucrose gradient purification.
Figure 1:
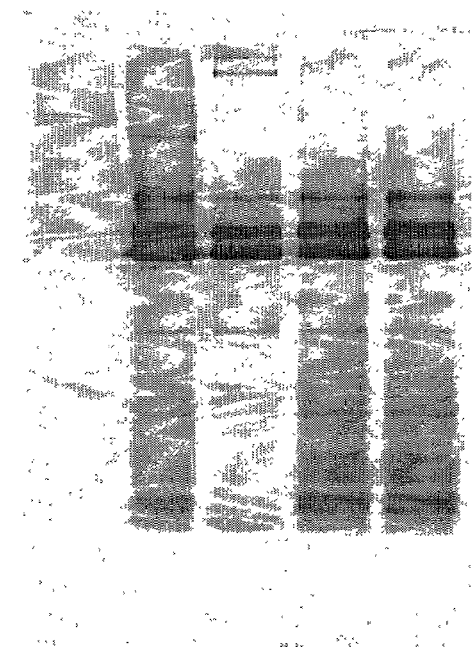

An object of the invention is to provide a purified RRV antigen substantially free of contaminants derived from the cell culture medium and the cells of the cell culture, such as cellular proteins and cellular nucleic acid, wherein the purified antigen is used in a vaccine particularly suitable for human clinical use in a host protective amount.

The term "cellular nucleic acid" means a heterogeneous DNA or RNA derived from the cells that have been infected with the virus to propagate the virus.

By "purified Ross River Virus antigen" is meant greater than about 97% purity as determined by SDS-PAGE and Western blot analysis with anti-cellular protein specific antibodies and quantification of residual cellular nucleic acid.

The term "substantially free" means that the amount of contaminating proteins derived from the cells or the cell culture or contaminating cellular nucleic said amount being below the detection limit of the state of the art detection method. Westernblot analysis and densitometric determination are used to test the amount of contaminating cellular proteins. A highly sensitive PCR method as described in U.S. Pat. No. 5,858,658 for nucleic acid quantification, particular for genomic VERO cell DNA, is used to quantify residual cellular nucleic acid in preparation.

The term "suitable for human clinical use" means that the endotoxin content for 10 μg antigen is less than about 2 IU, as determined by the chromogenic LAL test. In addition the level of DNA/μg protein antigen in the vaccine dose is less than about 50 pg, preferably less than about 20 pg, more preferably less than about 10 pg/μg antigen. Furthermore, the level of cellular contaminants per dose of virus antigen is less than about 0.1% of the total protein content, preferably less than about 0.05%, preferably below the detection limit of highly sensitive analysis method such as Western blot analysis with specific antibodies or HPLC analysis.

The "host protective amount" means the critical protective dose of viral antigen in the vaccine, wherein said amount is effective to immunize a susceptible mammal against Ross River Virus infection and induces a protective immune response in the host.

In accomplishing these and other objects of the present invention, there are provided in one aspect of the invention a method for the production of purified Ross River Virus antigen. This method comprises the steps of infecting a cell culture of cells with Ross River Virus, incubating said cell culture to propagate said virus, harvesting the virus produced, and filtering the harvested virus.

The cells used for infection of the virus can be any cell which is susceptible to RRV. According to one aspect of the invention the cells are a continuous cell line of monkey kidney cells, such as VERO cells or CV-1 cells. VERO cells are available from the American Tissue Cell Culture, deposited as ATCC CCL81.

Some substances like serum and serum-derived additives that can contaminate the final harvested viral antigen may either be derived from the cell culture medium or the cells. Conventional cell culture media comprise serum or protein additives such as albumin, transferrin or insulin, and other proteins or polypeptides derived from the serum or added to the cell culture medium during cell growth.

According to one embodiment of the invention the cells are grown in a serum free medium. The medium can be a minimal medium, such as DMEM or DMEM HAM's F12 and other minimal media known in the art, such as described in Kistner et al. (1998. Vaccine 16:960–968), which do not comprise any serum additives.

In a preferred embodiment of the invention the cells are grown in a serum and protein free medium prior to infection as described in WO 96/15213, WO 00/0300 or WO 01/23527, whereby said minimal medium can be supplemented with extracts of yeast or soy peptone.

The cells can be bound to microcarrier during cell culture growth. The microcarrier can be a microcarrier selected from the group of microcarriers based on dextran, collagen, plastic, gelatine and cellulose and others as described in Butler (1988. In: Spier & Griffiths, Animal cell Biotechnology 3:283–303). Therefore, according to one embodiment of the invention the serum free or serum and protein free cells are cultivated and infected on microcarriers. Preferably, the microcarrier is selected from the group of smooth surface microcarriers such as CYTODEX I microcarrier, CYTODEX II microcarrier and CYTODEX III microcarrier, and CYTOPORE microcarrier or CYTOLINE microcarrier (all Pharmacia). Preferably, the microcarrier are selected from the group of smooth surface such as Cytodex I®, Cytodex II® and Cytodex III®, Cytopore® or Cytoline® (all Pharmacia).

The cells bound to microcarrier are infected with RRV at a multiplicity of infection (m.o.i.) between about 0.001 and about 5.

Various conventional methods, such as chromatography, gradient centrifugation etc. are known in the art to remove contaminating proteins from the biological that is desired to be isolated and purified. Efficient purification methods often comprise several steps and combinations of filtration, ion exchange chromatography and gradient centrifugation. However, the various methods may reduce the virus titer and antigen yield during each purification step.

Filtration is used in the art to purify biological material, e.g. to remove contaminating agents, or during preparation of virus-free blood products to remove potential contaminating viruses, whereby viruses, particular enveloped-viruses, remain in the retenate, and the virus titer in the filtrate is reduced.

It has been surprisingly found by the present invention that by filtering the cell culture supernatant derived from cells infected with enveloped viruses (e.g., the Ross River virus), the enveloped virus passes the filter system without reduction of virus titer, while cellular contaminants, like proteins and nucleic acid are efficiently removed. The method of the invention provides purification of a high titer virus preparation by filtration, wherein this method is easily applicable for large-scale purification and efficiently removes most of the protein derived from the host cells as well as of cellular nucleic acid. The method of the invention therefore provides a process of purifying virus antigen by filtering without remarkable loss of virus titer and virus antigen.

The methods of the invention can be used to purify any enveloped viruses. Exemplary viruses include, Alphaviruses (e.g., Ross River Virus, Eastern equine encephalitis Virus, Venezuelan equine encephalitis, Western equine encephalitis, Sindbis Virus, Semiliki Forest Virus); Flaviviruses (e.g., St. Louis encephalitis Virus, Japanese encephalitis Virus, Dengue Virus, Yellow fever Virus, Tick-borne encephalitis Virus); Orthomyxoviruses (e.g., Influenza Virus); and Paramyxoviruses (e.g., New Castle Disease Virus).

According to one aspect of the methods of the invention, the filtering is performed on a filter having a pore size between about 0.3 and about 1.5 μm, which is preferably a filter based on a positively charged matrix. According to another aspect of the invention the filtering is performed on a filter having a pore size between about 0.1 and about 0.5 μm, which is preferably based on a hydrophilic matrix.

According to a preferred embodiment the filtering is performed by a combination of at least two filters, a first having a pore size of between about 0.3 and about 1.5 μm, and a second filter having a pore size of between about 0.1 and about 0.5 μm. The combination of the filtering steps can be performed with a first filtering step on a filter having a pore size of between about 0.3 and about 1.5 μm and the second filtering on a second filter having a pore size of between about 0.1 and about 0.5 μm. The filtering by a combination of filters can be performed either sequentially or in separate steps. The filter can be a filter such as a positively charged depth filter having a pore size of about 0.3 to about 1.5 μm and a hydrophilic filter having a pore size of about 0.22 μm. Any filtration system known in the art can be used as well. By filtering during virus/virus antigen purification, substantially all cellular protein contamination is removed. The cellular contaminating nucleic acid is also efficiently removed by a factor of at least 35, and an intermediate pure preparation having a purity of at least about 97% compared to the starting virus harvest is obtained by this purification step.

The filter used can be based a cellulose fiber matrix, hydrophilic filters, such as based on polyvinylidene fluoride membrane, or filters based on polypropylene membrane. Such filters are commercial available, e.g., ZETAPLUS filters (CUNO), DUIRAPORE filters. MILLIPAK filters or MILLIDISK filters (Millipore), or filters from Pall.

The method of the invention as described above therefore provides for a purified Ross River Virus antigen which is substantially free of contaminating proteins and nucleic acid from the cells or the cell culture. The preparation has a purity of at least about 97% compared to the starting material.

Another aspect of the present invention relates to a method for production of a purified Ross River Virus comprising the steps of infecting a cell culture of cells with Ross River Virus, incubating said cell culture to propagate said virus, harvesting the virus produced, filtering the harvested virus, treating the virus filtered with a nucleic acid degrading agent and purifying the virus.

The virus preparation obtained after filtering is treated with a nucleic acid degrading agent to destroy the structural integrity of the nucleic acid by breaking down residual nucleic acid that have not been removed by filtering. The degradation of the nucleic acid ensures that higher molecular weight nucleic acids are broken down to molecules of lower molecular weight, which are then removed during the final purification step.

The nucleic acid degrading agent according to the invention can be an enzyme which degrades nucleic acid, preferably a nucleic acid degradation enzyme, such as a nuclease, having DNase and RNase activity, or an endonuclease, such as from *Serratia marcescens*, commercial available as BENZONASE endonuclease (Benzon Pharma A/S). Most preferably the nucleic acid degradation agent is BENZONASE endonuclease.

The virus treated with a nucleic acid degradation agent can be further treated with an inactivating agent. The inactivating agent can be any agent with inactivating activity known in the art, such as e.g. formalin, BEI, laser light, UV light, chemical treatment such as methylene blue, psoralen, carboxyfullerene (C60), or a combination of any thereof as described in the prior art (Rowland et al. (1972). Arch. Ges. Virusforsch. 39:274–283; Mowat et al (1973). Arch. Ges. Virusforsch. 41:365–370, Rweyemamu et al. (1989). Rev. Sci. tech. Off. Int. Epiz. 8:747–767 and WO 01/46390). Other known methods in the art for inactivating viruses can be used as well.

The treatment of the virus with the nucleic acid degrading and inactivating agent can be performed by a sequential treatment or in a combined/simultaneous manner, whereby the purified virus antigen is treated with a combination of Benzonase as nucleic acid degrading agent and formalin or UV or BEI or a combination of formalin/BEI or formalin/UV as inactivation agent. The nucleic acid degrading agent is preferably added to the virus preparation prior the addition of the inactivation agent and during the course of the inactivation process, the nucleic acid degrading agent can be further added subsequently, if necessary.

According to another embodiment of the method of the invention the inactivated virus is further purified. The method therefore comprises after the step of nucleic acid degradation/virus inactivation treatment a further step to remove the nucleic acid degrading agent and the inactivating agent from the virus preparation. This can be performed by any method known in the art, such as chromatography, gel filtration or gradient centrifugation. According to one embodiment of the invention gradient purification, such as sucrose gradient centrifugation is preferred. This final purification step also removes the break-down products of the nucleic acid treatment with nucleic acid degrading agent and removes the residual nucleic acid and proteins that have not been removed by the filtering.

The preparation obtained with this method comprising Ross River virus antigen, wherein said preparation is substantially free of contaminating proteins derived from the cells or the cell culture and has less than about 50 pg cellular nucleic acid/µg virus antigen, preferably less than about 20 pg and most preferred less than about 10 pg cellular nucleic acid/µg virus antigen. Purified Ross River Virus antigen obtained is free of contaminating proteins and nucleic acid, suitable for human clinical use and is stable.

Another aspect of the invention provides a method for production of a vaccine comprising purified, inactivated Ross River Virus antigen comprising the steps of infecting a cell culture of cells with Ross River Virus, incubating said cell culture to propagate said virus, harvesting the virus produced, filtering the harvested virus, treating the filtered virus preparation with a nucleic acid degrading agent and virus inactivating agent, purifying the virus and formulating the purified and inactivated virus in a vaccine composition. According to one embodiment of the invention the method provides for a vaccine comprising purified Ross River Virus antigen and being substantially free of contaminating proteins and nucleic acids.

According to another aspect the invention provides for a preparation comprising purified Ross River Virus antigen being substantially free of contamination from the cells or cell culture.

According to another aspect the invention provides for a preparation comprising purified Ross River Virus antigen being substantially free of contaminating proteins from the cells or cell culture. The preparation has less than about 50 µg cellular nucleic acid/pg virus antigen, preferably less than about 10 pg nucleic acid/µg virus antigen. According to one embodiment of the invention the preparation comprises a physiologically acceptable carrier, such as a phosphate or Tris-based buffer.

In accordance with another aspect of the invention, there is provided a vaccine against Ross River Virus infection comprising a host protective amount of Ross River Virus antigen in an amount of between 0.1 to 50 µg antigen/dose, preferably between 0.3 and 30 µ.g antigen/dose. The antigen can be a whole virus or a fragment of the virus, such as a peptide or polypeptide, having an immunogenic epitope to induce protective antibodies against RRV infection. In a preferred embodiment of the invention the vaccine comprises as RVV antigen as whole inactivated virus.

The vaccine of the present invention comprising highly purified RRV can further comprise an adjuvant. It has been found that the presence of an adjuvant increases the immunogenicity of the purified antigen of the invention by inducing higher titers of neutralizing, protective antibodies when compared to a vaccine composition which does not comprise an adjuvant. The beneficial effect of the present vaccine may be due the higher purity of the RRV antigen used in the vaccine. The adjuvant may be aluminum or a salt thereof, mineral oils, Freund adjuvant, vegetable oils, water-in-oil emulsion, mineral salts, immunomodulator, immunopotentiator or other well known adjuvant know in the art at a desired concentration to increase the immune response e.g. to stimulate the production of neutralizing antibodies. The amount of adjuvant is well within the level of skill.

In a preferred embodiment of the invention, the adjuvant is aluminum or a salt thereof, such as aluminum hydroxide or aluminum phosphate. The aluminum concentration is preferably between 0.001% and 1% (w/v) per dose. The vaccine may be formulated in the most varying manner.

The vaccine may be administered in any known manner e.g. subcutaneously, intramuscularly or intraperitoneally. According to a preferred embodiment the vaccine is administered intramuscularly in a vaccination scheme in humans of 0, 1, 6 or 12 months or in a rapid immunization scheme for travelers of about 0, 14 and 28 days with a higher antigen dose per immunization and booster.

Another aspect of the invention provides for a method of immunizing a mammal against Ross River Virus infection comprising the steps of providing a vaccine comprising a host protective amount of purified Ross River Virus antigen and having an amount of cellular DNA of less than 10 pg/µg antigen, and wherein said vaccine is substantially free of any contaminating protein from the cells or the cell culture and administering said vaccine to a mammal.

According to a further aspect of the invention there is provided a method for the preparation of an immune globulin preparation comprising antibodies specific against Ross River Virus. The preparation comprising the immune globulins is obtained by immunizing a mammal with a Ross River Virus Vaccine as described above and isolating from the serum of the immunized mammal the immune globulin fraction comprising the RRV specific antibodies. The immune globulin fraction can be isolated by conventional method known in the art, such a Cohn fractionation and ion exchange chromatography.

These and other aspects of the invention disclosed herein will become apparent to he skilled artisan in view of the disclosure contained herein.

EXAMPLE 1

Production of Purified, Inactivated Ross River Virus Antigen a) Production of Ross River Virus on Serum and Protein Free VERO Cell Culture VERO cells (African Green Monkey, *Cercopthecus aethiops*, kidney) are used as a production cell line. The cells are been obtained from the American Type Cell Culture Collection, Rockville, Md. at a passage number 124 under the designation ATCC CCL 81. The cells are adapted to grow in serum or protein free medium as described in Kistner et al., 1998 (supra) or WO 96/15231. For growth in serum free medium a basal DMEM HAM's F12 medium supplemented with inorganic salts, amino acids, sodium bicarbonate and yeast extract is used. The working cell bank is prepared without the use of any animal derived medium components. Cells of the working cell bank are expanded in T-flasks and roller bottles with a split ration of 1:6. Further propagation of the cells is performed in a stirred tank bioreactor using CYTODEX microcarrier as attachment substrate. The cells are grown at 37° C. The culture conditions of oxygen saturation 20%+/−10% and pH7.25+/−0.35 are kept constant during virus propagation process. A serum free cell culture system of VERO cells as described by Kistner et al., (Vaccine 16:960–968 (1998) is infected with Ross River Virus at a multiplicity of infection (m.o.i.) of 0.001. After an incubation time of 3 days at 37° C. the fermenter is harvested and virus is recovered from the cell culture supernatant. The harvested virus gave a titer of 8.0 $TCID_{50}$/ml after removal of microcarriers and cell debris by centrifugation (about 9000 g).

b) Purification of RRV

The harvested virus is purified by filtering on a combination of a 1.2 µm filter ZETAPLUS filter, CUNO) and a 0.22 µm filter (DURAPORE filter, Millipore). The efficacy of the filtering to remove soluble proteins derived from the cell culture, in particular from VERO cells, is determined by Western blot analysis with VERO cell protein specific antibodies (FIG. 1A). FIG. 1 impressively shows that the filtering removes substantially all VERO cell derived proteins from the virus preparation.

Determination of virus titer of the virus harvest before filtering is 8.0 $TCID_{50}$/ml and after the filtering 7.4 $TCID_{50}$/ml (Table 1) revealed that during the filtering step substantially no virus antigen is lost. Detection of RRV antigen by Western blot analysis with RRV specific antibodies of the same samples as used for detection of VERO cell protein (FIG. 1B) showed that similar amounts of virus antigen is found in all samples tested during the various purification steps, indicating no loss of virus antigen during purification.

The amount of VERO cell DNA is determined by PCR as described in U.S. Pat. No. 5,858,658 is determined after each purification step and summarized in Table 1. The results show that during the filtering step the contaminating cellular nucleic acid is removed by a factor of at least 35.

After the filtering, BENZONASE endonuclease (2000 U/l) is added to the virus harvest to digest residual VERO cell and viral nucleic acid. During the following BENZONASE endonuclease treatment the residual contaminants are removed with by a factor of at least 2.

TABLE 1

Determination of Virus titer and contaminating nucleic acid during Ross River Virus antigen purification process

| Purification step | Virustiter ($TCID_{50}$/ml) | Total Protein amount (µg/ml) | Vero cell DNA (pg/ml) | DNA/Protein (pg/µg) |
|---|---|---|---|---|
| Harvest | 8.0 | 86 | $54 \times 10^4$ | 6.300 |
| Separator | 7.6 | 81 | $34 \times 10^4$ | 4.200 |
| Filtration 1.2 µm/0.2 µm | 7.2 | 80 | $14 \times 10^3$ | 175 |
| Benzonase | 7.4 | 85 | $7 \times 10^3$ | 82 |
| Sucrose gradient | inactivated | 180 | $1 \times 10^3$ | 5.5 |

After 1 h incubation at 37° C. with BENZONASE endonuclease, formalin, as a virus inactivation agent with an end concentration of 0.1% (w/v), is added for total inactivation time of 120 h at 37° C. 24 hours after the addition of formalin, BENZONASE endonuclease (1000 U/l) is added again. Filtration steps on 0.22 µm sterile filter (Millipore) are performed at 0, 2, 6, 24, 48, 72, 96, 120, 144, 168 and 192 hours and samples for virus titration and safety experiments are drawn in parallel.

The virus titration is carried out on VERO cells by determination of the tissue culture infectious dose 50 ($TCID_{50}$). Safety tests for demonstration of complete virus inactivation are carried out on C6–36 cells because they are about 10–100 times more susceptible for infection susceptible for infection with RRV than VERO cells.

The preparation comprising the inactivated virus is subjected to large scale flow zonal centrifugation over a 0–50% sucrose gradient to remove residual formalin, benzonase and nucleic acid break down products derived from the benzonase treatment. The sucrose gradient purification of inactivated virus resulted in one peak at sucrose concentration between 40% and 42%, demonstrating a pure and homogeneous antigen preparation. The fractions containing the virus are pooled and subjected to a 0.2 μm sterile filtration step.

The overall reduction during the purification process after sucrose-gradient therefore allowed reduction of contaminating nucleic acid by at least 4 log steps. The final purified RRV preparation contained about 5.5 pg cellular DNA/μg virus antigen. The isolated preparation of RRV antigen has a purity of at least 98% with regard to cellular contaminants. The final purity of this preparation with regard to nucleic acid is also given in Table 1.

EXAMPLE 2

Characterization of RRV

The inactivated RRV preparation of Example 1 is adjusted to a protein concentration of 10 μg/ml. The endotoxin content, determined by LAL-assay, is less than 1.50 EU/ml. The pyrogenicity test is performed according to European Pharmacopoeia 2001, 2.6.8. A temperature increase of greater than 2.65° C. is considered as pyrogen, and smaller than 1.15° C. as pyrogen free. The amount of VERO cell DNA is determined by PCR as described in U.S. Pat. No. 5,858,658. The amount of residual VERO cell DNA in the preparation is far below the limit required by the WHO for biologicals produced in continuous cell lines (CCLs), i.e. 10 ng per dose (1998, WHO, Technical Report Series No. 878). The results of the characterization of purity of the inactivated RVV preparation is shown in Table 2.

TABLE 2

Analysis of RRV Vaccine

| Test | Result |
|---|---|
| Dose/Antigen | 10 μg |
| LAL | <1.50 EU/ml |
| Pyrogenicity | 0.50° C. (pyrogen free) |
| VERO cell DNA | 50 pg |

EXAMPLE 3

Immunogenicity of the RRV Vaccine

Determination of the Effective Dose ($ED_{50}$) of antigen is performed by adjusting the RRV antigen concentration to 10 μg/dose, without and with $Al(OH)_3$ as an adjuvant at concentration of 0.05%, 0.1% and 0.2% (w/v). The candidate vaccine preparation is then diluted in 4 fold steps. Each dilution is injected into a group of 10 CD1 mice. After 4 weeks, the mice are boostered with the respective amount of antigen. Blood samples are drawn at 4 weeks, before the booster, and at 6 weeks after the booster. The sera of the samples are analyzed by a RRV-antibody ELISA and the $ED_{50}$ is calculated. Table 3 shows the $ED_{50}$ of the vaccine with and without adjuvant. To induce an immune response with similar antibody titers, in the vaccine comprising an adjuvant only 1/5 to 1/20 of the amount of antigen of the vaccine with adjuvant is needed, depending on the adjuvant concentration used. The increasing the adjuvant concentration in the final preparation allows reduction of virus antigen amount in the vaccine. This is in contrast to prior art results of Yu et al. and Aaskov et al. (supra), which had showed negative influence of adjuvant on protective antibody induction.

TABLE 3

Effective Dose ($ED_{50}$) and Protective Dose ($PD_{50}$) of RRV Vaccine in mice

| $ED_{50}$ Antigen (ng) 4 weeks | $ED_{50}$ Antigen (ng) Booster 6 weeks | $PD_{50}$ Antigen (ng) 6 weeks | Adjuvant $Al(OH)_3$ |
|---|---|---|---|
| 413 | 150 | 1250 | — |
| 83 | 2 | 20 | 0.05% |
| 74 | 9 | 20 | 0.1% |
| 20 | 7 | 20 | 0.2% |

The sera of the mice used for determination of $ED_{50}$ are also analyzed in terms of their neutralizing activity. The neutralization assay is performed by diluting infectious virus in 10 fold steps and incubated either with buffer or with heat-inactivated 1:10 dilutions of mouse serum for 1 hour at RT. The virus dilutions are subjected to a plaque assay on VERO cells to determine the virus titer. The neutralization index or ratio of virus titer in buffer as control versus virus titer incubated with mouse serum is calculated. The results show that less antigen in the vaccine composition comprising adjuvant is needed to induce higher Neutralization Titer (NT) compared to the vaccine containing adjuvant.

Determination of Protective Dose ($PD_{50}$) is performed in that half of the immunized mice of each group used in the previous experiment which are challenged at week 6 and 2 weeks after booster with $10^6$ $TCID_{50}$ of infectious RRV. The results of the experiment show that 50% of the mice being infected with infectious RRV have not developed a viraemia at the respective antigen dose. These results are given in Table 3.

These results show that the presence of an adjuvant in the vaccine did not effect the induction of a protective immune response. Even more, the vaccine preparation of the present invention allowed a drastic reduction of the antigen content in the vaccine dose of up to 1/20 in the presence of an adjuvant compared to the vaccine without adjuvant. Therefore, the vaccine preparation of the present invention differed in regard to purity and capability to induce protective immune response in the presence of adjuvant from those known in the prior art.

Accordingly, the amount of protective dose for larger mammal will be in the range between 0.1 and 50 μg antigen/protective dose depending on the average body weight of the mammal.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method for production of purified Ross River Virus antigen, comprising the steps of infecting a cell culture with Ross River Virus; incubating said cell culture to propagate said virus; harvesting the virus produced; filtering the harvested virus with a first filter having a pore size of between 0.3 and 1.5 μm; filtering the harvested virus with a second filter having a pore size of between 0.1 and 0.5 μm; and purifying the virus antigen.

2. The method according to claim 1, wherein the cell culture comprises VERO cells that have been grown in serum free medium.

3. The method according to claim 1, wherein said second filtering step is PERFORMED on a filter having a pore size of about 0.2 µm.

4. The method according to claim 1, wherein the first and second filtering steps reduce cellular protein and nucleic acid contaminants.

5. A method far the production of a purified Ross River Virus preparation, comprising the steps of infecting a cell culture with Ross River Virus; incubating said cell culture to propagate said virus; harvesting the virus produced; filtering the harvested virus with a first filter having a pore size of between about 0.3 and about 1.5 µm; filtering the harvested virus with a. Second filter having a pore size of between 0.1 and 0.5 µm; treating the filtered virus with a nucleic acid degrading agent; and purifying the virus.

6. The method according to claim 5, wherein the cell culture comprises VERO cells that have been grown in a serum free medium.

7. The method according to claim 5, wherein said second filtering step is performed on a filter having a pore size of about 0.2 µm.

8. The method according to claim 5, wherein the nucleic acid degrading agent is an enzyme having DNase and Kinase activity.

9. The method according to claim 5, wherein said filtered virus is further treated with a virus inactivating agent.

10. The method according to claim 5, wherein said preparation is substantially free of contaminating proteins from said cell culture and has less than about 10 pg cellular nucleic acid/µg virus antigen.

11. A method for production of an immunogenic composition comprising purified, inactivated Ross River Virus antigen, comprising the steps of infecting a cell culture with Ross River Virus; incubating said cell culture to propagate said virus; harvesting the virus produced; filtering the harvested virus with a first filter having a pore size of between about 0.3 and about 1.5 µm; filtering the harvested virus with a second filter having a pore size of between 0.1 and 0.5 µm; treating the filtered virus with a nucleic acid degrading agent and a virus inactivating agent; purifying the virus; and formulating the purified virus in an immunogenic composition.

12. The method of claim 11, wherein said first filter is based on a positively charged matrix and said second filter is based on a hydrophilic matrix.

13. The method of claim 1, further comprising treating the filtered virus with a nucleic acid degrading agent.

14. The method of claim 1, wherein said first filter is based on a positively charged matrix and said second filter is based on a hydrophilic matrix.

15. The method of claim 5, wherein said first filter is based on a positively charged matrix and said second filter is based on a hydrophilic matrix.

16. A method according to any of claims 1, 5, or 11 wherein the method is used for large scale production.

* * * * *